United States Patent [19]

Veits

[11] Patent Number: 5,744,634
[45] Date of Patent: Apr. 28, 1998

[54] PROCESS FOR PRODUCING 2-KETO-L-GULONIC ACID ESTERS

[75] Inventor: Joachim Veits, Rheinfelden, Germany

[73] Assignee: Roche Vitamins Inc., Parsippany, N.J.

[21] Appl. No.: 858,639

[22] Filed: May 19, 1997

Related U.S. Application Data

[63] Continuation of Ser. No. 349,159, Dec. 2, 1994, abandoned.

[30] Foreign Application Priority Data

Jan. 18, 1994 [CH] Switzerland ............... 154/94

[51] Int. Cl.$^6$ .................................... C07C 69/66
[52] U.S. Cl. ........................... 560/174; 560/186
[58] Field of Search .......................... 560/186, 174

[56] References Cited

U.S. PATENT DOCUMENTS 5,128,487  7/1992  Tomislav et al. ............. 549/315

FOREIGN PATENT DOCUMENTS

| 0138436 | 4/1985 | European Pat. Off. . |
| 0403351 | 12/1990 | European Pat. Off. . |
| 0535927 | 9/1992 | European Pat. Off. . |
| 1260927 | 1/1972 | Germany . |

OTHER PUBLICATIONS

Chemical Abstract 64:12784C.
English Abstract for EP# 0 403 351.
Drefahal, J. Prakt. Chem. Bd. 1, pp. 153–156 (1955).
T.A. Melentyeva, et al. Chemical Abstracts, 271553f vol. 119, No. 25 (1993).
Derwent Abstract Basic No. 19,401 (1965).
Gao et al, Kinetics of esterification of 2 keto L gulonic acid with methanol on ion exchange resin catalyst, Fudan Xuebao, Ziran Kexueban (1986) 25(2) 163 8.

*Primary Examiner*—Gary Geist
*Assistant Examiner*—Rosalynd Keys
*Attorney, Agent, or Firm*—George W. Johnston; William H. Epstein; Lewis J. Kreisler

[57] ABSTRACT

A process for the manufacture of methyl or ethyl 2-keto-L-gulonate by esterifying 2-keto-L-gulonic acid with methanol or ethanol continuously in the presence of an acidic ion exchanger in the temperature range between room temperature and about 80° C. and with average residence times between about 10 and about 120 minutes and with superficial velocities of about 0.5 m/h to about 7.5 m/h. The esterification is advantageously carried out under slight over-pressure. The thus-manufactured esters are important intermediates for the synthesis of vitamin C and the respective esterification product can be converted directly into vitamin C by lactonization.

7 Claims, 1 Drawing Sheet

PROCESS FOR PRODUCING 2-KETO-L-GULONIC ACID ESTERS

This is a continuation of application Ser. No. 08/349,159 filed Dec. 2, 1994, abandoned.

BACKGROUND OF THE INVENTION

The esterification of 2-keto-L-gulonic acid with a lower alkanol, especially methanol, is known from numerous publications. One such esterification is usually carried out in the presence of an acidic catalyst, e.g. hydrochloric acid, sulphuric acid or p-toluenesulphonic acid. After the esterification to the corresponding lower alkyl ester, this lower alkyl ester can be subjected to an alkaline rearrangement (or lactonization) to produce ascorbic acid or a salt thereof, usually the sodium or potassium salt.

Occasional references to the esterification of 2-keto-L-gulonic acid in the presence of an ion exchanger as the acidic catalyst are found in the technical literature. However, in most cases details of yields, conversions etc. are missing or the reported results, e.g. with respect to yields and crystal quality, are unsatisfactory. Moreover, these processes require long reaction times and often high reaction temperatures. A process for the continuous esterification of 2-keto-L-gulonic acid has hitherto not been carried out or has not been published.

Basically, an esterification process for the manufacture of a 2-keto-L-gulonic acid ester, especially the methyl or ethyl ester, should be simple to carry out, gentle and should proceed with high conversion (produce high yields), and be a continuous procedure.

Such an esterification process which fulfils the stated requirements to a high degree and which has advantages over conventional processes has now been found. The process in accordance with the invention for the esterification of 2-keto-L-gulonic acid with methanol or ethanol to its methyl or ethyl ester comprises carrying out the esterification continuously in the presence of an acidic ion exchanger in the temperature range between room temperature and about 80° C. and with average residence times between about 10 and about 120 minutes and with superficial velocities of about 0.5 m/h to about 7.5 m/h (h=hour), optionally under slight over-pressure.

SUMMARY OF THE INVENTION

The present invention is concerned with a novel process for the manufacture of 2-keto-L-gulonic acid esters. As is known, these esters are important intermediates for the synthesis of ascorbic acid (vitamin C). This process comprises esterifying 2-keto-L-gulonic acid with methanol or ethanol continuously in the presence of an acidic ion exchanger at temperatures from about room temperature to about 80° C. and with average residence times from about 10 to about 120 minutes, and with superficial velocities of about 0.5 m/h to about 7.5 m/h, optionally under slight over-pressure.

DETAILED DESCRIPTION OF THE INVENTION

Figure 1:
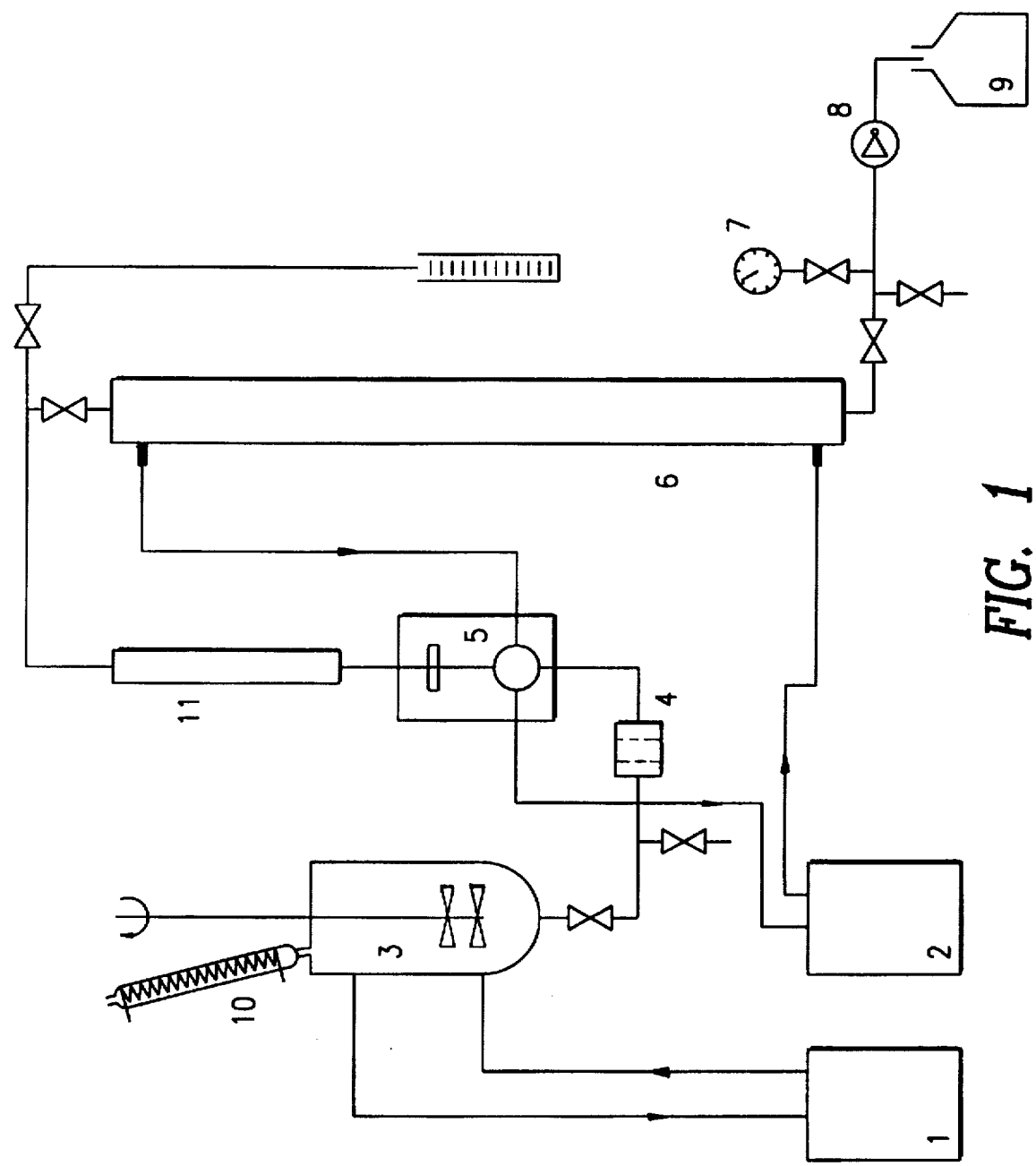
FIG. 1 is a schematic representation depicting the apparatus used for esterifying 2-keto-L-gulonic acid in accordance with the invention.

This invention is directed to a novel process for esterification of 2-keto-L-gulonic acid (2-KLGA) with methanol or ethanol. This process comprises esterifying 2-KLGA with methanol or ethanol continuously in the presence of an acidic ion exchanger at temperatures from about room temperature to about 80° C., with average residence times from about 10 minutes to about 120 minutes and with superficial velocities of about 0.5 m/h to about 7.5 m/h, optionally under slight over-pressure.

Essentially, the esterification is carried out by allowing a solution of 2-keto-L-gulonic acid in methanol or ethanol to continuously flow over the acidic ion exchanger situated in a reactor, such as depicted as (6) in FIG. 1. The esterification is generally carried out in the temperature range from about room temperature to about 80° C. with average residence times in the reactor from about 10 to 120 minutes. Best results are obtained at temperatures from about 55° C. to about 65° C., and with average residence times from about 10 to about 120 minutes. With regard to overall conversion of 2-keto-L-gulonic acid to an ester, it is generally true that higher temperatures necessitate shorter average residence times. Moreover, the esterification taking place in the reactor is conveniently effected under a slight over-pressure up to a maximum of 4 bar, independently of the esterification temperature. With regard to the overall conversion, there is a slight dependence on the esterification temperature and the concentration of 2-keto-L-gulonic acid in the methanol or ethanol. For example, with concentrations in the range of about 8 to about 15 weight percent of 2-keto-L-gulonic acid in methanol the esterification proceeds (almost) ideally at about 60° C. and with residence times of less than 20 minutes. Under such conditions the residual 2-keto-L-gulonic acid content is normally a maximum of 1%.

In general, the esterification in accordance with the invention is carried out with concentrations of about 2.5 to about 15 weight percent of 2-keto-L-gulonic acid in methanol or ethanol. When methanol is used, the concentration conveniently lies in the range of 8 to 15 weight percent (wt./wt. %), which corresponds to a concentration, expressed in weight/volume percent (wt./vol. %), of 7 to 14 wt./vol. % based on anhydrous 2-keto-L-gulonic acid. The 2-KLGA to be esterified can be used as anhydrous or hydrated 2-keto-L-gulonic acid (especially the monohydrate form). The anhydrous form is, however, preferred. It has been found that, at least in the concentration range 8 to 12.2 wt./wt. % of the 2-keto-L-gulonic acid in methanol, the esterification proceeds practically independently of the concentration: the course of the reaction in this concentration range is almost constant (zero or pseudo-zero order reaction with respect to the 2-keto-L-gulonic acid).

In the above definition of the invention the term "acidic ion exchanger" embraces any acidic ion exchanger known in the art, such as the commercially available DUOLITE® C 20, C 26, C 264 and C 265 (all Rohm & Haas); AMBERLITE® 18 wet and IRA 120 (also Rohm & Haas); AMBERLYST® 15 (Rohm & Haas); LEWATIT® S 100 and SP 112 (Bayer); as well as DOWEX® ion exchanger I (Dow). AMBERLYST® is the best suited of these acidic ion exchangers for the purpose of the present invention. Basically, any other acidic ion exchangers can, of course, also be used in accordance with this invention to esterify 2-KLGA with methanol or ethanol.

The term "superficial velocity" which also appears in the definition of the invention is known in the art and denotes the flow velocity with which a liquid reaction mass, i.e., 2-KLGA in methanol or ethanol, flows through a tube-like or column-like reactor filled with the acidic ion exchanger and which, as explained hereinafter, depends on the throughput volume and on the cross section of the reactor tube. This velocity is connected in the wider sense with the average effective velocity. This is expressed mathematically as follows:

$$\text{Superficial velocity} \ (V_{superficial}) = \frac{\text{Throughput volume } [cm^3 \text{ or } m^3]}{\text{tube cross section } [cm^2 \text{ or } m^2] \times \text{time } [h]}$$

in which $V_{superficial}$ is expressed as cm/h or m/h.

As mentioned above, the superficial velocity $V_{superficial}$ is directly connected with the so-called average effective velocity $V_{effective}$, namely according to the equation:

$$V_{effective} = \frac{V_{superficial}}{e}$$

in which $e$ (void fraction) $= \frac{V_R - V_C}{V_R}$ ($V_R$ = reactor volume; $V_C$ = catalyst volume)

These terms are explained in more detail inter alia in the textbook "Thermische Verfahrenstechnik" by A. Mersmann, p. 99 et seq., Springer-Verlag Berlin Heidelberg, New York 1980.

As mentioned above, the superficial velocity is, inter alia, an essential feature of the invention. When it has a range of about 0.5 m/h to about 7.5 m/h, this corresponds to an average effective velocity of about 0.9 to about 14.5 m/h.

A typical installation for the esterification process in accordance with the invention is shown schematically in FIG. 1, with the given dimensions applying to a small scale plant. On a commercial scale appropriately larger dimensions will, of course, apply.

The process in accordance with the invention has several advantages, namely:

- the procedure is continuous and accordingly is efficient to carry out;
- the residence times are relatively short in comparison to previous esterifications of 2-keto-L-gulonic acid with methanol or ethanol;
- the practical (with respect to apparatus) performance of the process is simple and economical, especially, for example, because neither water removal for equilibrium displacement nor high reaction temperatures are required;
- the corrosion of a metal-containing reaction vessel is avoided, since the catalyst used to carry out the esterification is not a mineral acid, e.g. hydrochloric acid, sulphuric acid etc.;
- the equilibrium conversions are high, the product having, depending on the specific reaction conditions, a residual unreacted 2-keto-L-gulonic acid content of only about 0.5 to 1.5 weight percent; and
- the esterification product can be used directly, i.e. without isolating the methyl or ethyl 2-keto-L-gulonate, in the lactonization step for the manufacture of the desired ascorbic acid, e.g. under alkaline conditions (using, for example, sodium bicarbonate, sodium hydroxide, sodium methoxide or trihexylamine as the base).

The process in accordance with the invention also embraces various procedural variants of the above-described, relatively simple procedure with the object of increasing the nevertheless very high equilibrium conversion even more. For example, the reaction mixture can pass through several (two or more) interconnected reactors until the desired (especially high) conversion has been achieved. Further, after passage through a reactor a partial intermediate evaporation, i.e. partial removal of water with the same alkanol, e.g. methanol, can be carried out and the reaction mixture can subsequently be passed through a connected esterification column with or without the addition of fresh methanol or ethanol.

The process in accordance with the invention is illustrated on the basis of the following Examples, each of which refers to the aforementioned typical apparatus for esterification diagrammatically presented in FIG. I.

EXAMPLE 1

917.45 g of 2-keto-L-gulonic acid (hereinafter "2-KLGA"; 98.1% quality) and 10 L (liters) of methanol are introduced, in each case in 2 portions, into a 10 L glass vessel and stirred until a homogeneous solution has formed. The mixture is filtered clear over a 0.2 μm GELMAN membrane filter and the solution is transferred portionwise into the supply vessel (3). If desired, the supply vessel is heated at a temperature of 35° C. using a thermostat (1).

Then, the mixture is withdrawn via a bottom valve and pumped using a LEWA M8 membrane pump (5) with an input velocity of 800 ml/h firstly over a small pre-column (11) filled with AMBERLYST® 15 and thereafter through the exchanger bed situated in a double jacketed reactor (6) and heated to 60°–62° C. The filled pre-column has a protective function in that it captures traces of metal, e.g. iron, copper, zinc. etc. The heating of the column is effected at a temperature of 63° C. by means of a thermostat (2). In order to avoid boiling effects and the formation of gas bubbles, the apparatus is adjusted to 0.4–0.6 bar overpressure (7) with a pressure sustaining valve (8) installed at the column exit. In order to control the conversion, samples are withdrawn at intervals of 2 hours and in each case the residual 2-KLGA content is determined by HPLC. Parallel to this, a control of the input amount is performed using a graduated 50 ml shaking cylinder. Under the given conditions the superficial velocity is 2.86 m/h and the average effective velocity is 5.53 m/h. The average residence time is about 14.6 minutes.

After passage of the mixture a further 3 L of methanol are pumped through in order to rinse the apparatus.

In order to isolate the thus-manufactured methyl 2-keto-L-gulonate (hereinafter "Me-2-KLGA"), the esterification solution collected in the receiving vessel (9) is concentrated in a BÜCHI Rotavapor Type R 152 at a bath temperature of 50° C. and a pressure of 200 mbar to a crystal slurry (about 67 wt./wt. % Me-2-KLGA) and cooled at 40° C. for about 4 hours for further crystallization. The crystallizate is thereupon suction filtered over a sintered glass suction filter and rinsed twice with 500 ml of methanol (−10° C.) each time. Drying is effected at 50° C. and 10–15 mbar within 12 hours. Yield: 1700–1800 g of 1st cristallizate of Me-2-KLGA, quality≧99.5%.

In order to isolate the 2nd crystallizate, the mother liquor is likewise concentrated at 50° C. and 200 mbar to a crystal slurry (about 43 wt./wt. % Me2-KLGA content), cooled at 4° C. over 4 hours and the crystallizate is suction filtered over a sintered glass suction filter. Then, the product is rinsed twice with 130 ml of methanol (−10° C.) each time and dried at 50° C. under a vacuum for about 12 hours. Yield: about 100 g of 2nd crystallizate of Me-2-KLGA, quality>98.0%.

The overall conversion to Me-2-KLGA amounts to 97.5–97.9% (quantified by means of HPLC) starting from 2-KLGA and without the ascorbic acid formed as a byproduct, and 95.7–95.9% of theory of Me-2-KLGA are isolated as colourless crystals from the practically colourless esterification solution (1st and 2nd crystallizate, quality already considered).

Isolation of the crystals need not be effected, since the solution can be used, if desired, directly for the manufacture of ascorbic acid, e.g. by alkaline rearrangement (lactonization).

EXAMPLE 2

As described in Example 1, a 10.2 wt./wt. % solution of 2-KLGA in methanol is pumped through the column at a temperature of 30° C. and with a superficial velocity of 0.63 m/h and an average residence time of about 116 minutes. Conversion to a residual 2-KLGA content of about 5.1% takes place. A repeated passage of the solution under the same conditions, i.e. without intermediate partial removal of methanol/water, leads to a residual 2-KLGA content of about 1.6%.

EXAMPLE 3

As described in Example 1, a 10.2 wt./wt. % solution of 2-KLGA in methanol is pumped through the column at a temperature of 60°–62° C. and with a superficial velocity of about 5.7 m/h (corresponding to an average effective velocity of about 11 m/h) and a residence time of about 6.5 min. Conversion to a residual 2-KLGA content of about 7.3–9.1% takes place. A repeated passage of the solution under the same conditions leads to a residual 2-KLGA content of about 1.3–1.7%. The total residence time is thus 2× about 6.5 min., i.e. about 13 min.

EXAMPLE 4

Several 2-KLGA esterifications are carried out analogously to the procedure described in Example 1 under diverse conditions. The respective details are compiled in Table 1 hereinafter.

TABLE 1

Typical Examples/Results of esterification at 60–62° C. (ideal range)

| Concentration [wt./wt. %] | Residence time [min] | Superficial velocity [m/h] | Average effective velocity [m/h] | Residual 2-KLGA [%] |
|---|---|---|---|---|
| 8.2 | 29.0 | 1.27 | 2.45 | 0.42 |
|  | 19.5 | 1.91 | 3.69 | 0.42 |
|  | 14.5 | 2.54 | 4.91 | 1.40 |
| 10.2 | 23.5 | 1.59 | 3.07 | 0.63 |
|  | 16.7 | 2.23 | 4.31 | 0.65 |
|  | 14.6 | 2.86 | 5.53 | 0.80 |
|  | 13.0 | 3.50 | 6.77 | 0.96 |
| 12.2 | 29.0 | 1.27 | 2.45 | 0.91 |
|  | 19.5 | 1.91 | 3.69 | 1.00 |
|  | 14.5 | 2.54 | 4.91 | 1.32 |
| 15.0 | 29.0 | 1.27 | 2.45 | 0.90 |
|  | 19.5 | 1.91 | 3.69 | 1.10 |
|  | 14.5 | 2.54 | 4.91 | 1.35 |

EXAMPLE 5

Further 2-KLGA esterifications (Tests 1–6) are carried out analogously to the procedure described in Example 1. The average residence time in this case is about 14.6 min. and the superficial velocity is about 2.86 m/h. The other relevant details are compiled in Table 2 hereinafter:

TABLE 2

Batch: 1800 g of 2-KLGA gives 1929.6 g of Me-2-KLGA according to theory

| Notation (T = test) |  | T 1 | T 2 | T 3 | T 4 | T 5 | T 6 |
|---|---|---|---|---|---|---|---|
| 1. Residual 2-KLGA[1] | [%] | 0.82 | 0.86 | 0.70 | 0.85 | 0.85 | 0.82 |
| 2. 1st crystallizate Me-2-KLGA |  |  |  |  |  |  |  |
| Yield | [g] | 1678.9 | 1731.0 | 1752.8 | 1793.0 | 1818.6 | 1754.9 |
| Content | [%] | 99.5 | 99.8 | 99.6 | 98.5 | 99.4 | 99.4 |
| Amount (10 | [g] | 1670.1 | 1727.5 | 1745.8 | 1766.1 | 1807.7 | 1743.4 |
| Theoretical amount | [%] | 86.6 | 89.5 | 90.5 | 91.5 | 93.7 | 90.4 |
| 3. 2nd crystallizate Me-2-KLGA |  |  |  |  |  |  |  |
| Yield | [g] | 178.0 | 118.4 | 101.7 | 79.6 | 57.1 | 107.0 |
| Content | [%] | 98.0 | 98.8 | 96.8 | 94.3 | 94.0 | 96.4 |
| Amount (100%) | [g] | 174.4 | 117.0 | 98.4 | 75.1 | 53.7 | 103.7 |
| Theoretical amount | [%] | 9.0 | 6.1 | 5.1 | 3.4 | 2.8 | 5.4 |
| 4. Mother liquor 2 |  |  |  |  |  |  |  |
| Me-2-KLGA content | [g] | 54.1 | 40.5 | 44.1 | 27.4 | 40.4 | 41.3 |
| Theoretical amount | [%] | 2.8 | 2.1 | 2.3 | 1.4 | 2.1 | 2.1 |
| 5. Balancing |  |  |  |  |  |  |  |
| Me-2-KLGA isolated. total (100%) | [g] | 1844.5 | 1844.5 | 1844.2 | 1841.2 | 1861.4 | 1847.2 |
| Theoretical amount | [%] | 95.6 | 95.6 | 95.6 | 95.4 | 96.5 | 95.7 |
| Amount of Me-2-KLGA. Total | [g] | 1898.6 | 1885.0 | 1888.3 | 1868.3 | 1901.8 | 1888.5 |
| Theoretical amount Total | [%] | 98.4 | 97.7 | 97.9 | 96.8 | 98.6 | 97.9 |

[1] These values were determined by standardization from the peak areas Me-2-KLGA, ascorbic acid and 2-KLGA.

I claim:

1. A process for the manufacture of methyl or ethyl 2-keto-L-gulonic acid ester comprising:
   reacting 2-keto-L-gulonic acid with a lower alkanol selected from the group consisting of methanol and ethanol to form a reaction mass, and
   exposing the reaction mass to an acidic ion exchanger to produce said ester, at a temperature from about room temperature to about 80° C. continuously for a time from about 10 minutes to about 120 minutes, wherein said exposing is characterized by flowing the reaction mass over the ion exchanger to produce a flow having a superficial velocity from about 0.5 m/h to about 7.5 m/h.

2. The process of claim 1, wherein the ion exchanger is AMBERLYST® 15.

3. A process of claim 1, wherein the exposing is carried out at temperatures from about 55° C. to about 65° C. continuously for a time from about 10 minutes to about 20 minutes.

4. A process of claim 1, wherein said exposing is carried out under an over-pressure up to maximum of 4 bar.

5. The process of claim 1, wherein the lower alkanol is methanol.

6. A process of claim 5, wherein the concentration of 2-keto-L-gulonic acid in methanol is in the range of from about 8 to about 15 weight percent.

7. The process of claim 6, wherein the exposing is carried out at a temperature about 60° C. for a time up to a maximum of 20 minutes.

* * * * *